United States Patent [19]

Balg

[11] 4,154,964

[45] May 15, 1979

[54] PROCESS FOR THE PURIFICATION OF A PHENOL

[75] Inventor: Theodorus Balg, Brunssum, Netherlands

[73] Assignee: Stamicarbon, B.V., Geleen, Netherlands

[21] Appl. No.: 832,950

[22] Filed: Sep. 13, 1977

[30] Foreign Application Priority Data

Sep. 24, 1976 [NL] Netherlands .......................... 7610598

[51] Int. Cl.² ............................................. C07C 37/24
[52] U.S. Cl. ................................................... 568/757
[58] Field of Search .......... 260/621 A, 621 G, 624 A, 260/627 R; 568/757, 810, 749, 801

[56] References Cited

U.S. PATENT DOCUMENTS

| | | | |
|---|---|---|---|
| 2,301,709 | 11/1942 | Rumscheidt et al. ................. | 568/757 |
| 2,727,926 | 12/1955 | Kaeding et al. ....................... | 568/801 |
| 2,727,928 | 12/1955 | Menn et al. ........................... | 260/624 A |
| 2,752,398 | 6/1956 | Riley ..................................... | 260/624 A |
| 3,410,318 | 7/1964 | Sodomann et al. .................. | 260/621 A |

FOREIGN PATENT DOCUMENTS 705919 3/1965 Canada ................................. 260/621 G

*Primary Examiner*—Werren B. Lone
*Attorney, Agent, or Firm*—Cushman, Darby & Cushman

[57] ABSTRACT

A process for the purification of a phenol compound prepared by decarboxylative oxidation of a benzoic acid to a phenol compound, including treating the phenol with a countercurrent flow of phosphoric acid and a temperature gradient to remove substituted and unsubstituted benzaldehyde and related compounds.

6 Claims, 1 Drawing Figure

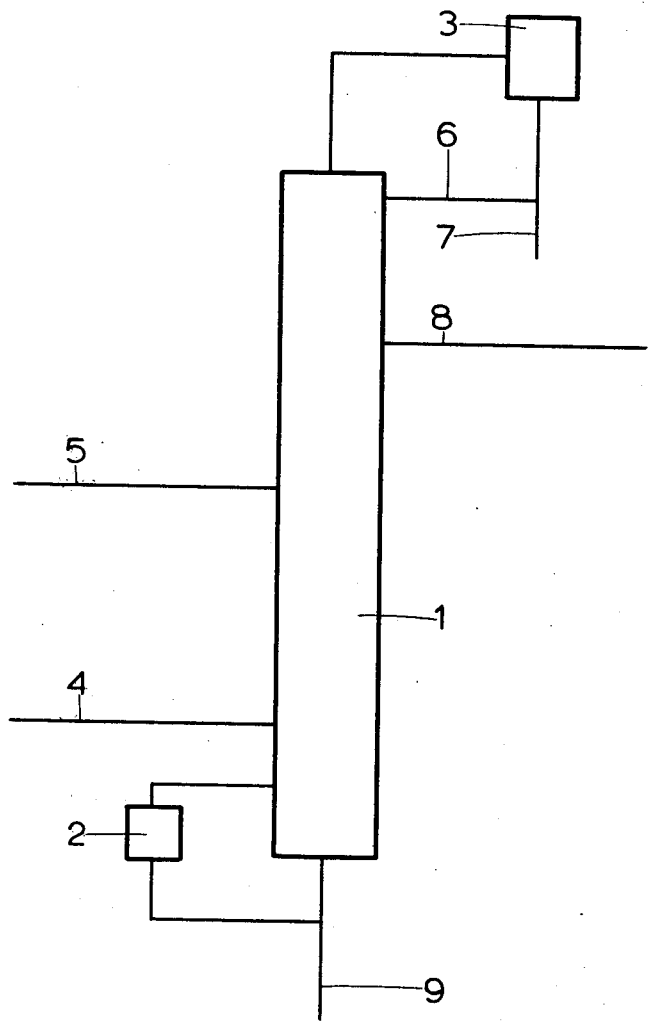

PROCESS FOR THE PURIFICATION OF A PHENOL

BACKGROUND OF THE INVENTION

The present application is related to Netherlands Patent Application No. 7610598, filed Sept. 24, 1976, the entire disclosure of which is hereby incorporated by reference.

Oxidation processes for the production of phenol from an alkyl benzene compound are described in the literature. In these processes an alkyl benzene compound is first oxidized to a corresponding benzoic acid, followed by decarboxylation-oxidation of the benzoic acid to a phenol compound. For example, it is known that toluene is readily oxidized to benzoic acid by passing air through liquid toluene in the presence of a catalyst at elevated temperatures and pressures. The oxidation of benzoic acid to phenol occurs when steam and air are passed through benzoic acid in the liquid phase in the presence of a catalyst. The phenol produced is carried out of the reaction vessel with the steam and air. Several detailed descriptions of these processes have been published. See Kirk-Othmer *Encyclopedia of Chemical Technology*, 2d rev. ed., vol. 15, pages 147, 155-156 (John Wiley 1968) and references cited therein.

The term "benzoic acid" as used in this specification include both substituted and unsubstituted benzoic acids, and salts, esters and anhydrides thereof. Similarly, the term "alkyl benzene compound" as used in this specification includes both substituted and unsubstituted alkyl benzene compounds, and the term "phenol" includes both substituted and unsubstituted phenols. For example, the following alkyl benzene compounds may be oxidized by the process described above to the indicated corresponding benzoic acids:

| Alkyl benzene compound | Benzoic acid |
| --- | --- |
| 1,2-Dimethylbenzene | 2-Methylbenzoic acid |
| 1,3-Dimethylbenzene | 3-Methylbenzoic acid |
| 4-Chlorotoluene | 4-Chlorobenzoic acid |

In the second step of the two-step oxidation process, the benzoic acid is subject to decarboxylation-oxidation to form the indicated phenol:

| Benzoic acid | Phenol |
| --- | --- |
| 2-Methylbenzoic acid | 3-Methylphenol |
| 3-Methylbenzoic acid | 2- and 4-Methylphenol |
| 4-Chlorobenzoic acid | 3-Chlorophenol and Phenol |

See, e.g., U.S. Pat. No. Re. 24,848 to Kaeding, which is hereby incorporated by reference.

The catalytic oxidation of the alkyl benzene compound to the corresponding benzoic acid may be conducted either in the liquid phase or in the gaseous phase. If the catalytic oxidation is conducted in the liquid phase, a cobalt salt which is soluble in the liquid phase is suitable as a catalyst. If the oxidation is carried out in the gaseous phase, a vanadium catalyst may be used. See Stanford Research Institute Reports No. 7, pages 29-33 (1965); No. 7A, pages 241-244 (1968); and No. 7B, pages 53-55 (1976), which are hereby incorporated by reference.

The decarboxylation-oxidation of the benzoic acid formed in the first step to the penol compound may, for example, be carried out in the liquid phase by reaction with molecular oxygen in the presence of a copper catalyst. In addition to the copper catalyst, a magnesium catalyst may also be present. Both the copper catalyst and the magnesium catalyst are preferably dissolved in the liquid reaction phase. Copper benzoate and magnesium benzoate are suitable catalysts. See *Hydrocarbon Processing*, volume 43, pages 173 ff. (November 1965), and the Stanford Research Institute Reports, No. 22, pages 147 ff. (1967) and No. 22A, pages 113 ff. (1972), which are hereby incorporated by reference.

The decarboxylation-oxidation reaction of the benzoic acid to the phenol compound can be effected by passing a gas containing molecular oxygen through a molten benzoic acid compound or a solution of a benzoic acid compound in an inert solvent, in the presence of a dissolved copper catalyst. The reaction is assisted by passing steam through the liquid reaction phase. The phenol product is carried out of the liquid reaction phase with the molecular oxygen containing gas, and steam. The phenol can then be separated from these gases.

It is also possible to carry out the decarboxylation-oxidation reaction in two steps by reacting the benzoic acid with molecular oxygen in a first step without the addition of steam, to form an ester of benzoic acid with the corresponding phenol. This ester of benzoic acid and the corresponding phenol can be hydrolyzed in a second step by reaction with steam. The phenol product is carried out of the reaction with the steam, and separated. The benzoic acid compound is returned to the first step.

A disadvantage of the above-described processes is that the phenol product obtained is nearly always contaminated with traces of substituted or unsubstituted benzaldehyde compounds and related compounds. The term 'benzaldehyde' will hereinafter be used to refer to the substituted or unsubstituted benzaldehyde compounds and related compounds which contaminate the phenol product of the above-described processes. The traces of benzaldehyde present in the phenol product are very difficult to remove, whereas commercially a phenol product low in benzaldehyde is desirable.

The purified phenol product may be subjected to hydrogenation to form cyclohexanols or cyclohexanones, depending upon the reaction conditions, as described in British Patent Specification No. 890,095. The cyclohexanols and cyclohexanones formed by hydrogenation of the purified phenol product of the present invention are easily separated, and are therefore of commercial importance.

SUMMARY OF THE INVENTION

Briefly, in accordance with the invention, a process is disclosed for the purification of a phenol compound prepared by decarboxylation-oxidation of benzoic acid. The phenol compound is purified by treatment with phosphoric acid in a plate or packed column in which there is a temperature gradient. The phosphoric acid enters an upper portion of the column, which is maintained at a relatively cool temperature. The phosphoric acid moves downwardly in the column, in countercurrent flow to the rising phenol and against the temperature gradient within the column. Purified phenol, free of benzaldehyde, is removed from an upper portion of the column.

Accordingly, it is an object of the present invention to provide a process for the purification of phenol which removes benzaldehyde from phenol produced by the decarboxylation-oxidation of benzoic acid.

Another object of the present invention is to provide a process for the purification of phenol which removes benzaldehyde from phenol produced by the decarboxylation-oxidation of benzoic acid without introducing any new contaminant.

Another object of the present invention is to provide a process for the purification of phenol which removes benzaldehyde from phenol produced by the decarboxylation-oxidation of benzoic acid by countercurrent treatment with phosphoric acid and a temperature gradient.

Yet, another object of the present invention is to provide a process for the purification of phenol which removes benzaldehyde from phenol produced by the decarboxylation-oxidation of benzoic acid without the necessity of using expensive corrosion-resistant equipment.

Other objects of the invention will be apparent from the description of the drawing, the detailed description of the invention and the claims which follow.

DESCRIPTION OF THE DRAWING

An embodiment of the process according to the present invention is illustrated in the drawing. In the drawing 1 is a plate column or a packed column fitted with a recycling evaporator 2 and a condenser 3. The column is fitted with either plates (not shown) to form a plate column or the column is fitted with packings (not shown) to form a packed column. A temperature gradient is maintained within the column such that upper portions of the column are progressively cooler.

The phenol to be purified is fed into column 1 from conduit 4. Phosphoric acid is fed into column 1 from conduit 5. The phosphoric acid moves downwardly in the column, in countercurrent relationship to the phenol which rises upwardly in the column, and against the temperature gradient.

Purified phenol is removed in the liquid state from the column 1 through conduit 8. Vapors passing through the top of column 1 are condensed in condenser 3. A portion of the condensate is returned to column 1 by conduit 6. The remaining condensate is discharged through 7 as a light fraction consisting of a somewhat less pure phenol.

A portion of the liquid passing through the bottom of column 1 is evaporated in recycling evaporator 2 and returned to column 1. The remaining liquid discharged through the bottom of column 1 is discharged through conduit 9 as a bottom product containing phosphoric acid.

DETAILED DESCRIPTION OF THE INVENTION

In the process of the present invention, a phenol compound prepared by decarboxylation-oxidation of benzoic acid is purified by treatment with phosphoric acid in a plate or packed column in which there is a temperature gradient. The phenol compound is preferably an unsubstituted phenol. However, any phenol compound produced by the decarboxylation-oxidation of either a substituted or unsubstituted benzoic acid may be purified by the process of the present invention. Examples of substituted phenols which may be purified by the process of the present invention include alkylphenol compounds and halophenol compounds. Preferred alkylphenol compounds include alkyl substituents having from one to about six carbons are especially suitable for purification by the process of the present invention. Preferred halophenols include chlorophenols prepared from chlorobenzoic acid and bromophenols prepared from bromobenzoic acid. Other substituted phenols such as nitrophenols, as well as disubstituted phenols such as 2,5-dimethylphenol may be purified by the process of the present invention.

The phenol compound to be purified is treated with a countercurrent flow of phosphoric acid and a temperature gradient. The phosphoric acid may be either orthophosphoric acid, metaphosphoric acid or pyrophosphoric acid. Orthophosphoric acid is, however, preferred in the practice of the present invention. For example, an 85% by weight aqueous solution of orthophosphoric acid, which is commercially available, may suitably be used in the practice of the present invention. The amount of phosphoric acid used to treat the phenol to be purified in the process of the present invention is not critical. A catalytic amount of phosphoric acid with respect to the phenol to be purified is sufficient. In particular, amounts of phosphoric acid from about 0.25 to about 25 grams of phosphoric acid per kilogram of phenol may suitably be used in the process of the present invention.

The plate column or packed column 1 may be a distillation column. If column 1 is a distillation column, the process of the present invention can easily be combined with purification of the phenol by distillation. Column 1 may be fitted with sieve plates or baffle plates, or other conventional plates to form a plate column. Alternatively, column 1 may be fitted with Raschig rings or Lessing rings or other conventional packings to form a packed column.

In general, the temperature of column 1 is maintained between about 100° and about 300° C. The pressure in column 1 is not critical and may vary between about 0.1 and about 10 atmospheres. A pressure in the column between about 1 and about 2 atmospheres is preferred in the practice of the present invention, with atmospheric pressure being especially preferred.

A temperature gradient is maintained within at least the portion of the column conduit 4 and conduit 5, with the temperature decreasing from conduit 4 to conduit 5. The difference in temperature between conduit 4 and conduit 5 is at least about 0.1° C., and preferably at least about 0.5° C. If column 1 is a distillation column, the difference in temperature between conduit 4 and conduit 5 will depend upon the pressure drop in column 1. At a larger pressure drop, the temperature difference will be larger. Although the difference in temperature between conduit 4 and conduit 5 may be very large, it is preferred that the difference in temperature be not more than about 10° C. If the pressure within column 1 is about atmospheric pressure, it is preferred that the difference in temperature between conduit 4 and conduit 5 be between about 0.5 and 2° C.

It is a particularly surprising and unexpected result of the process according to the present invention that benzaldehyde is removed from the phenol to be purified only if the phenol is treated with phosphoric acid in a countercurrent flow and against a temperature gradient as described. It is found that if phenol to be purified is treated with phosphoric acid not in the manner required in the present invention, it is much less effective with respect to removing benzaldehyde.

The present invention will now be illustrated with the aid of an Example, and two Comparative Experiments. It is, of course, understood that the present invention is not limited to the illustrated example, but includes all aspects of the invention as described above, and set forth in the claims which follow.

EXAMPLE 4.0 Kilograms of crude phenol per hour are fed to distillation column 1 through conduit 4 as illustrated in the Figure. The crude phenol was prepared by oxidation of toluene to benzoic acid, and subsequent decarboxylation-oxidation of the benzoic acid to phenol. The oxidation of toluene to benzoic acid was conducted in the liquid phase with molecular oxygen and a cobalt catalyst dissolved in the liquid phase. The decarboxylation-oxidation of benzoic acid to phenol was also conducted in the liquid phase using molecular oxygen and steam, and a copper catalyst dissolved in the liquid phase. The phenol produced was analyzed for benzaldehyde by reaction with 2,4-dinitrophenyl hydrazine for 50 minutes at 60° C. Thereafter, the reaction solution was cooled and diluted with a solution of potassium hydroxide in ethanol, and the extraction at 515 nm measured. The analysis of the phenol showed 220 mg, calculated as benzaldehyde, per kilogram of phenol produced by the process described.

An 85% by weight aqueous solution of orthophosphoric acid was fed into column 1 through conduit 5 at a rate of 10.7 grams of orthophosphoric acid per hour. The temperature in the column at conduit 5 was 182.9° C., while the temperature in the column at conduit 4 was 183.7° C. The phosphoric acid moved downwardly in the column, in countercurrent relationship to the rising phenol and against the temperature gradient described.

Purified phenol was removed from column 1 through conduit 8 at a rate of 3.6 kilograms per hour. The purified phenol thus produced in accordance with the present invention was analyzed for benzaldehyde by the method described above. The benzaldehyde analysis showed that the purified phenol product contained 35 mg of benzaldehyde per kilogram of purified phenol.

COMPARATIVE EXPERIMENT A

The procedure of the above Example was repeated, except that the phosphoric acid was fed into column 1 together with the phenol through conduit 4 instead of conduit 5. Purified phenol removed from column 1 through conduit 8 was analyzed for benzaldehyde as described above. The analysis showed that the purified phenol contained 90 mg of benzaldehyde per kilogram of phenol.

COMPARATIVE EXPERIMENT B

The procedure of the Example was again repeated, but no phosphoric acid was fed into column 1. Purified phenol was withdrawn from column 1 through conduit 8 and analyzed for benzaldehyde as described above. The analysis showed the purified phenol contained 130 mg of benzaldehyde per kilogram of purified phenol.

Thus, it is apparent that there has been provided, in accordance with the invention, a process for the purification of a phenol compound that fully satisfies the objects, aims, and advantages set forth above. While the invention has been described in conjunction with a specific embodiment thereof, it is evident that there are many alternatives, modifications and variations which will be apparent to those skilled in the art in light of the foregoing description. Accordingly, it is intended to embrace all such alternatives, modifications, and variations as fall within the spirit and broad scope of the following claims.

What is claimed is:

1. A process to purify a phenol compound prepared by decarboxylation-oxidation of a benzoic acid, said phenol compound selected from unsubstituted phenols, alkylphenols with alkyl substituents from about one to about six carbons, chlorophenols, bromophenols, and nitrophenols, comprising:

feeding said phenol compound in a lower portion of a column maintained at a temperature of between about 100° C. and about 300° C., whereby said phenol compound flows upwardly in said column, feeding phosphoric acid into an upper portion of said column maintained at a temperature not more than about 10° C. lower than the temperature of said lower portion of said column thereby maintaining a temperature gradient in said column, whereby said phosphoric acid flows downwardly in said column in countercurrent relationship to said phenol compound flow and against said temperature gradient, contacting said phenol compound in said column with said countercurrent flow of phosphoric acid against said temperature gradient and removing the purified phenol compound from said column.

2. The process of claim 1, wherein said column is a distillation column.

3. The process of claim 2 wherein said phenol is contacted with said phosphoric acid with simultaneous purification of said phenol compound by distillation.

4. The process of claim 1, wherein said phosphoric acid is an aqueous solution of phosphoric acid.

5. The process of claim 4, wherein said aqueous solution of phosphoric acid is an aqueous solution of orthophosphoric acid.

6. The process of claim 1, wherein said temperature of said upper portion of said column is between 0.5° C. and 2° C. lower than said temperature of said lower portion of said column.

* * * * *